United States Patent
Lai et al.

(10) Patent No.: US 11,906,376 B2
(45) Date of Patent: Feb. 20, 2024

(54) FORCE SENSOR FOR TENDON-ACTUATED MECHANISMS

(71) Applicant: Nanyang Technological University, Singapore (SG)

(72) Inventors: Wenjie Lai, Singapore (SG); Lin Cao, Singapore (SG); Soo Jay Louis Phee, Singapore (SG)

(73) Assignee: Nanyang Technological University, Singapore (SG)

( * ) Notice: Subject to any disclaimer, the term of this patent is extended or adjusted under 35 U.S.C. 154(b) by 667 days.

(21) Appl. No.: 17/054,744

(22) PCT Filed: May 22, 2019

(86) PCT No.: PCT/SG2019/050271
§ 371 (c)(1),
(2) Date: Nov. 11, 2020

(87) PCT Pub. No.: WO2019/226119
PCT Pub. Date: Nov. 28, 2019

(65) Prior Publication Data
US 2021/0223123 A1     Jul. 22, 2021

(30) Foreign Application Priority Data
May 22, 2018    (SG) ............................ 10201804332S

(51) Int. Cl.
*G01L 1/24*     (2006.01)
*G01L 5/00*     (2006.01)
(Continued)

(52) U.S. Cl.
CPC .............. *G01L 1/246* (2013.01); *A61B 34/71* (2016.02); *G01L 5/0033* (2013.01); *G01L 5/105* (2013.01); *A61B 2090/064* (2016.02)

(58) Field of Classification Search
CPC ......... G01L 1/24; G01L 5/0033; G01L 5/103; A61B 34/71; A61B 2090/064
See application file for complete search history.

(56) References Cited

U.S. PATENT DOCUMENTS

| | | | |
|---|---|---|---|
| 7,930,065 | B2 | 4/2011 | Larkin et al. |
| 8,075,498 | B2 | 12/2011 | Leo et al. |

(Continued)

FOREIGN PATENT DOCUMENTS

| | | |
|---|---|---|
| CN | 206258205 U | 6/2017 |
| WO | 2016149819 A1 | 9/2016 |
| WO | 2019226119 A1 | 11/2019 |

OTHER PUBLICATIONS

Foreign Communication from a Related Counterpart Application, Chinese Office Action dated Nov. 16, 2021, Chinese Application No. 201980031826.5 filed on May 22, 2019.
(Continued)

*Primary Examiner* — Kristina M Deherrera
*Assistant Examiner* — Jean F Morello

(57) ABSTRACT

A force sensor for a tendon-actuated mechanism, the force sensor comprising: a body having a through hole for passage of a tendon of the tendon-actuated mechanism therethrough, the body configured to be connected to a part of the tendon-actuated mechanism through which the tendon passes; and a sensor provided on the body to obtain a compression force on the body from the part of the tendon-actuated mechanism through which the tendon passes.

14 Claims, 8 Drawing Sheets

(51) Int. Cl.
*G01L 5/105* (2020.01)
*A61B 34/00* (2016.01)
*A61B 90/00* (2016.01)

(56) References Cited

U.S. PATENT DOCUMENTS

| | | | |
|---|---|---|---|
| 8,182,433 | B2 | 5/2012 | Leo et al. |
| 8,298,227 | B2 | 10/2012 | Leo et al. |
| 8,374,670 | B2 | 2/2013 | Selkee |
| 8,622,935 | B1 | 1/2014 | Leo et al. |
| 8,808,311 | B2 | 8/2014 | Heinrich et al. |
| 8,882,660 | B2 | 11/2014 | Phee et al. |
| 8,932,288 | B2 | 1/2015 | Leo et al. |
| 8,945,095 | B2 | 2/2015 | Blumenkranz et al. |
| 9,186,046 | B2 | 11/2015 | Ramamurthy et al. |
| 9,204,830 | B2 | 12/2015 | Zand et al. |
| 9,561,031 | B2 | 2/2017 | Heinrich et al. |
| 9,855,662 | B2 | 1/2018 | Morales et al. |
| 10,111,722 | B2 * | 10/2018 | Poon ................ A61B 34/37 |
| 2003/0036748 | A1 | 2/2003 | Cooper et al. |
| 2007/0078484 | A1 | 4/2007 | Talarico et al. |
| 2009/0123111 | A1 | 5/2009 | Udd |
| 2010/0298844 | A1 | 11/2010 | Blumenkranz |
| 2013/0096572 | A1 | 4/2013 | Donhowe et al. |
| 2014/0051987 | A1 | 2/2014 | Kowshik et al. |
| 2014/0180168 | A1 * | 6/2014 | Millett ................ A61B 5/6852 600/587 |
| 2015/0018840 | A1 | 1/2015 | Monfaredi et al. |
| 2016/0296122 | A1 | 10/2016 | Kim et al. |
| 2017/0156928 | A1 | 6/2017 | He et al. |
| 2017/0303824 | A1 | 10/2017 | Schlesinger et al. |

OTHER PUBLICATIONS

Foreign Communication from a Related Counterpart Application, International Search Report and Written Opinion dated Aug. 13, 2019, International Application No. PCT/SG2019/050271 filed on May 22, 2019.
S. Ehrampoosh, M. Dave, M. A. Kia, C. Rablau, and M. H. Zadeh, "Providing haptic feedback in robot-assisted minimally invasive surgery: A direct optical force-sensing solution for haptic rendering of deformable bodies," Computer Aided Surgery, vol. 18, pp. 129-141, Sep. 1, 2013 2013.
A. M. Okamura, "Haptic Feedback in Robot-Assisted Minimally Invasive Surgery," Current opinion in urology, vol. 19, pp. 102-107, 2009.
Y. Kobayashi, P. Moreira, C. Liu, p. Poignet, N. Zemiti, and M. G. Fujie, "Haptic feedback control in medical robots through fractional viscoelastic tissue model," in 2011 Annual International Conference of the IEEE Engineering in Medicine and Biology Society, 2011, pp. 6704-6708.
T. N. Do, T. Tjahjowidodo, M. W. S. Lau, and S. J. Phee, "A new approach of friction model for tendon-sheath actuated surgical systems: Nonlinear modelling and parameter identification," Mechanism and Machine Theory, vol. 85, pp. 14-24, Mar. 1, 2015 2015.
M. Kaneko, T. Yamashita, and K. Tanie, "Basic considerations on transmission characteristics for tendon drive robots," in Advanced Robotics, 1991. 'Robots in Unstructured Environments', 91 ICAR., Fifth International Conference on, 1991, pp. 827-832 vol. 1.
L. Chen and X. Wang, "Modeling of the tendon-sheath actuation system," in 2012 19th International Conference on Mechatronics and Machine Vision in Practice (M2VIP), 2012, pp. 489-494.
P. Puangmali, K. Althoefer, L. D. Seneviratne, D. Murphy, and P. Dasgupta, "State-of-the-Art in Force and Tactile Sensing for Minimally Invasive Surgery," IEEE Sensors Journal, vol. 8, pp. 371-381, 2008.
A. A. G. Abushagur, N. Arsad, M. Ibne Reaz, A. Ashrif, and A. Bakar, "Advances in Bio-Tactile Sensors for Minimally Invasive Surgery Using the Fibre Bragg Grating Force Sensor Technique:A Survey," Sensors (Basel, Switzerland), vol. 14, pp. 6633-6665, 2014.
K. O. Hill and G. Meltz, "Fiber Bragg grating technology fundamentals and overview," Journal of Lightwave Technology, vol. 15, pp. 1263-1276, 1997.
P. S. Zarrin, A. Escoto, R. Xu, R. V. Patel, M. D. Naish, and A. L. Trejos, "Development of an optical fiber-based sensor for grasping and axial force sensing," in 2017 IEEE International Conference on Robotics and Automation (ICRA), 2017, pp. 939-944.
Z. Wang, Z. Sun, and S. J. Phee, "Haptic feedback and control of a flexible surgical endoscopic robot," Computer Methods and Programs in Biomedicine, vol. 112, pp. 260-271, Nov. 1, 2013 2013.
J. O. Zhi Zhou, "Techniques of temperature compensation for FBG strain sensors used in long-term structural monitoring," 2004.

* cited by examiner

FORCE SENSOR FOR TENDON-ACTUATED MECHANISMS

CROSS-REFERENCE TO RELATED APPLICATIONS

The present application is a filing under 35 U.S.C. 371 as the National Stage of International Application No. PCT/SG2019/050271, filed May 22, 2019, entitled "FORCE SENSOR FOR TENDON-ACTUATED MECHANISMS," which claims priority to Singapore Application No. SG 10201804332S filed with the Intellectual Property Office of Singapore on May 22, 2018, both of which are incorporated herein by reference in their entirety for all purposes.

FIELD

This invention relates to a force sensor for tendon-actuated mechanisms such as a tendon-sheath mechanism (TSM) or a tendon-driven mechanism.

BACKGROUND

In tendon-actuated medical-use robots and devices, there are generally two ways to realize force/haptic feedback: 1) tip force prediction through modelling [5-8]; 2) tip force measurement by directly mounting sensors on surgical instruments [9-13, 16-25]. Since change in the route configuration of the flexible robot varies the parameters of models, it is challenging to acquire accurate real-time tip forces purely based on proximal data. Comparatively, the second way is preferred and brings significant benefits to both surgeons and patients [2-4]. However, electrical sensors (such as piezoelectric sensor, MEMS, strain gauge sensors, and thin film) require electrical wiring, and face problems such as requiring force decoupling (i.e. between different force directions and between elongation and bending of the tendon) leading to design complexity, replacement difficulties, noise from electromagnetic interference, need for signal amplification, risk of damage due to exposure to biological tissue or the working environment and so on [14], particularly for endoscopic robots [1]. There is therefore a need for a force sensor for tendon-actuated mechanisms that requires no need for force decoupling, is simple to connect, is electrically passive, is compatible for use on and within the human body, is preferably compatible for use with magnetic resonance imaging (MRI) and preferably also able to be miniaturized for endoscopic use.

SUMMARY

Disclosed is a force sensor for a tendon-actuated mechanism. The force sensor may comprise a body having a through hole (such as a Nitinol or nickel-titanium tube) and a Fibre Bragg Grating (FBG) fibre attached to the body at the FBG segment of the FBG fibre. The body is configured to be attached to a part of the tendon-actuated mechanism through which the tendon passes. The force sensor may be compactly and efficiently implemented for tendon-actuated mechanisms such as a tendon-sheath driven mechanism (TSM) as the body may comprise a tubular structure provided with a similar diameter and hollow configuration as the sheath of a TSM. The body may extend from one end of the sheath, and a tendon goes or passes through the sheath as well as the through hole in the body. Pulling on the tendon results in compression of the sheath which transmits a compression force to the body and thus produces strain on the FBG strain sensor. By recording the wavelength shift of the FBG due to the strain, the compression force on the body from the sheath, which equals the tension force magnitude on the tendon (theoretically and experimentally verified), can be obtained. In addition to detecting the distal end force, the disclosed force sensor can be used to sense haptic information at the proximal end or in-between the tendon-actuated mechanism as well. The force sensor can also be applied to sense haptic information in tendon-driven continuum robots or flexible robots. Furthermore, instead of being locating at the furthest distal end of a sheath, the sensor can alternatively be located in-between a sheath or between two sheaths, which is more compact and has less restriction for the sensor length and size. The force sensor has abundant advantages such as small size, high sensitivity and resolution, dismountability, multi-mechanism transferability, temperature compensation, flexibility, easy-fabrication, compact integration, biocompatibility, MRI compatibility, and sterilizability. The force sensor can also be applied for a variety of other tendon-actuated mechanisms such as robotic fingers/hands, wearable devices, surgical catheters, and rehabilitation devices.

According to a first aspect, there is provided a force sensor for a tendon-actuated mechanism, the force sensor comprising: a body having a through hole for passage of a tendon of the tendon-actuated mechanism therethrough, the body configured to be connected to a part of the tendon-actuated mechanism through which the tendon passes; and a sensor provided on the body to obtain a compression force on the body from the part of the tendon-actuated mechanism through which the tendon passes.

The sensor may comprise an optical fibre having a first Fibre Bragg Grating (FBG) segment, the first FBG segment being attached to the body, and wherein shift in wavelength of light transmitted by the first FBG segment is directly correlatable to the compression force on the body.

The optical fibre may have a second FBG segment, wherein in use, the second FBG segment is not attached to any part of the tendon-actuated mechanism and shift in wavelength of light transmitted by the second FBG segment is directly correlatable to a difference in temperature experienced by the second FBG segment.

The first FBG segment may be attached to an outer surface of the body.

Grating length of the first FBG segment may be less than or equal to 1 mm.

The body may be made of a deformable material.

The body may be provided with perforations to improve flexibility of the body.

The body may comprise a tubular structure.

The tendon-actuated mechanism may comprise a tendon-sheath mechanism and the body is collinearly attached to a sheath of the tendon-sheath mechanism.

The tendon-sheath mechanism may comprise at least two sheaths and wherein the body of the force sensor is provided between the at least two sheaths.

The tendon-actuated mechanism may comprise a continuum robot, the continuum robot comprising a plurality of disks and a number of tendons passing through the plurality of disks, at least some of the number of tendons each terminating in a stopper, wherein for at least one of the number of tendons terminating in a stopper, the body of the force sensor is provided between the stopper and a disk that is immediately adjacent the stopper.

According to a second aspect, there is provided a method of determining a force on a tendon-actuated mechanism, the method comprising:

a) providing a force sensor on a part of the tendon-actuated mechanism through which a tendon of the tendon-actuated mechanism passes; and
b) obtaining with the force sensor a compression force on a body of the force sensor from the part of the tendon-actuated mechanism through which the tendon passes.

Step a) may comprise passing the tendon through a through hole in the body and connecting the body with the part of the tendon-actuated mechanism through which the tendon passes.

The force sensor may comprise an optical fibre having a first Fibre Bragg Grating (FBG) segment attached to the body, and step b) may comprise obtaining a shift in wavelength of light transmitted by the first FBG segment and correlating the shift in wavelength of light transmitted by the first FBG segment to magnitude of the compression force on the body.

The method may further comprise:
c) providing a second FBG segment not attached to any part of the tendon-actuated mechanism;
d) obtaining a shift in wavelength of light transmitted by the second FBG segment;
e) correlating the shift in wavelength of light transmitted by the second FBG segment to a difference in temperature experienced by the second FBG segment; and
f) offsetting the shift in wavelength of light transmitted by the first FBG segment with the shift in wavelength of light transmitted by the second FBG segment to compensate for difference in temperature experienced by the first FBG segment.

For both aspects, the compression force may be comparable to a tension force on the tendon.

BRIEF DESCRIPTION OF FIGURES

In order that the invention may be fully understood and readily put into practical effect there shall now be described by way of non-limitative example only exemplary embodiments of the present invention, the description being with reference to the accompanying illustrative drawings.

DETAILED DESCRIPTION

Figure 1:
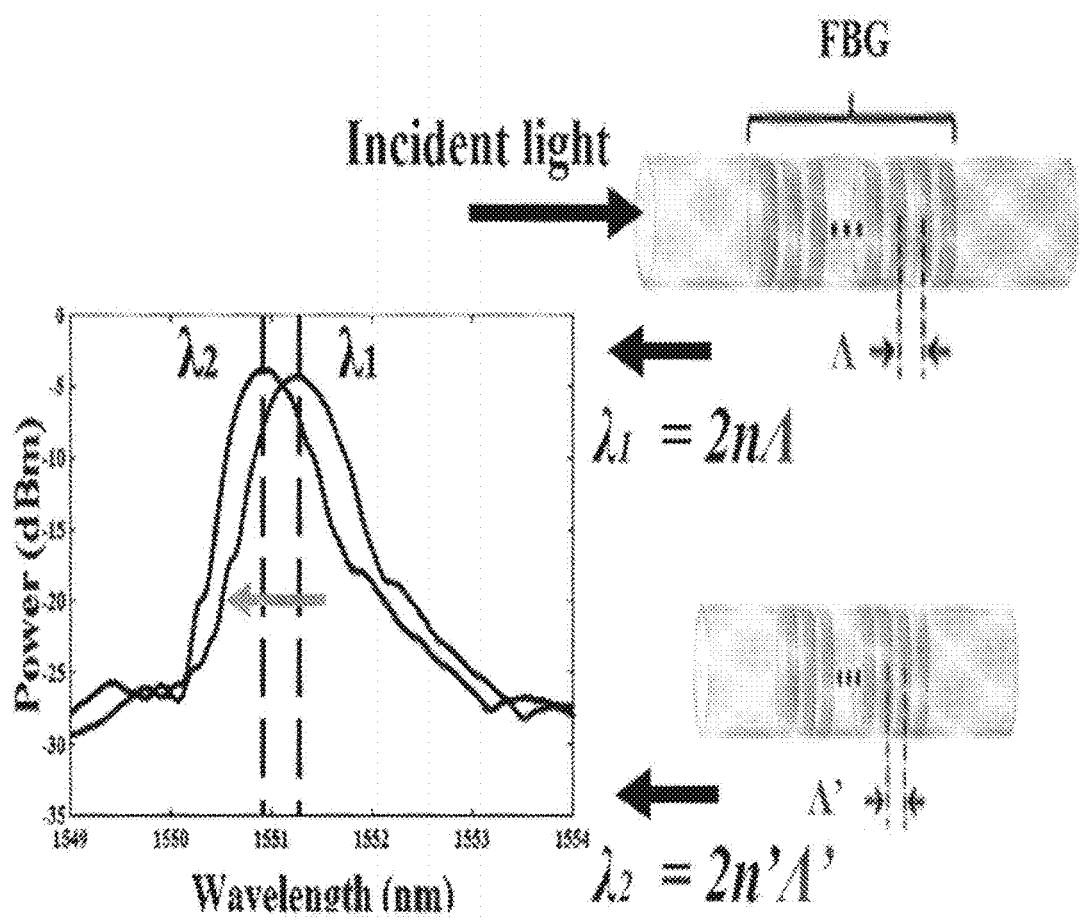
FIG. 1 is an illustration of FBG working principle.

Exemplary embodiments of a force sensor 10 for tendon-actuated mechanisms will be described below with reference to FIGS. 1 to 15. The same reference numerals are used throughout the figures for the same or similar parts.

A Fibre Bragg Grating (FBG) is a type of distributed Bragg reflector constructed in a short segment of an optical fibre. With a periodic variation in the refractive index of the fibre core, FBG is capable of reflecting a particular band of light that shifts in response to variations in temperature and/or strain, as shown in FIG. 1. The central wavelength of the reflection band is called Bragg wavelength ($\lambda_B = 2n_{eff}\Lambda$), where $n_{eff}$ represents the effective refractive index of the fibre core mode and $\Lambda$ is the core refractive index modulation [15]. The parameters $n_{eff}$ and $\Lambda$ are dependent on temperature and strain. The change of the axial strain along the fibre can cause the central wavelength to shift linearly, which offers an effective way of measuring the loading force by tracking the Bragg wavelength.

Figure 2:
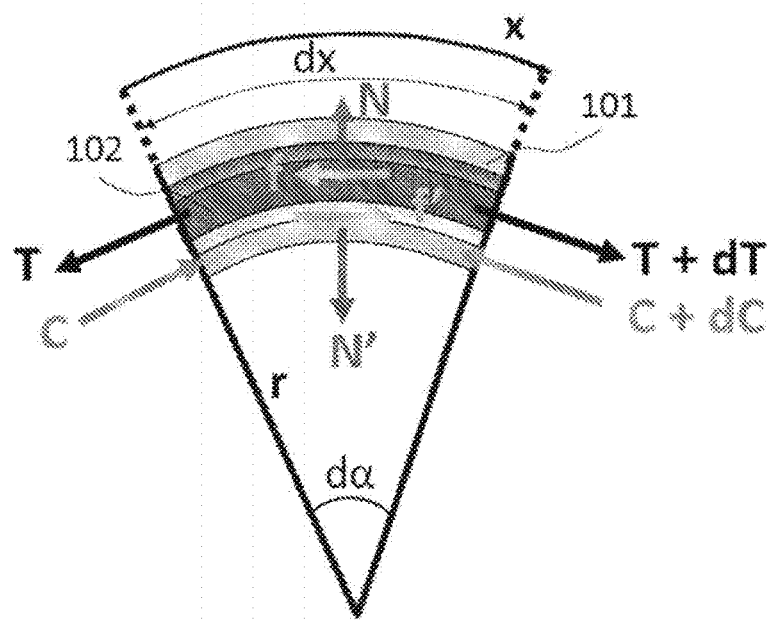
FIG. 2 is a schematic longitudinal sectional view of an infinitesimal segment of a tendon-sheath mechanism.
Figure 3:
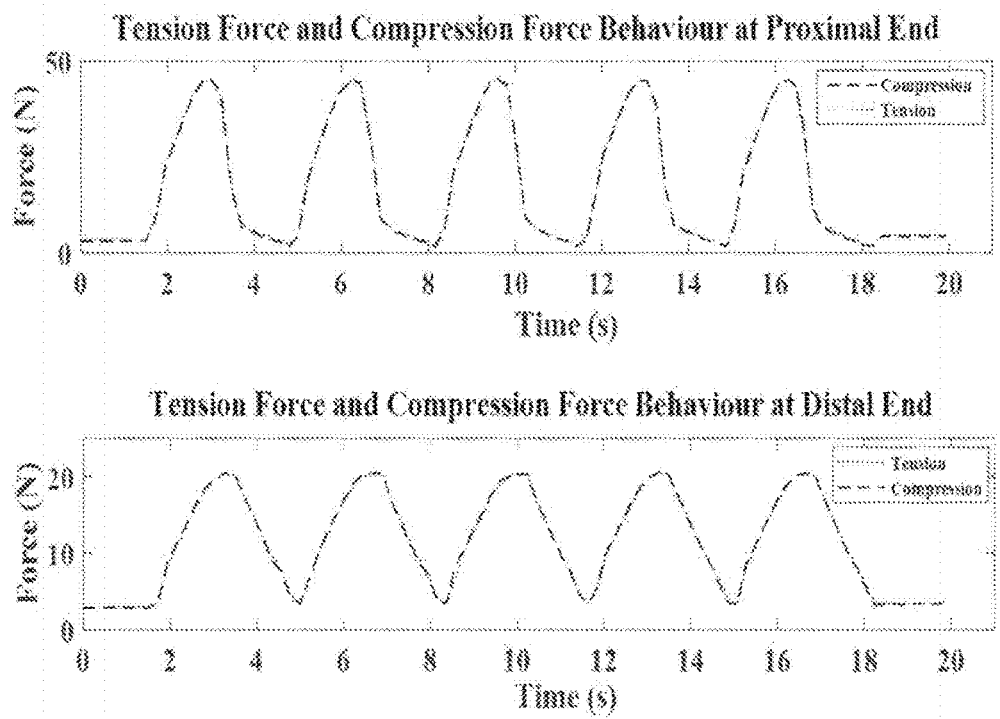
FIG. 3 shows graphs of test results from experiments performed to determine tension forces on a tendon and compression forces on a sheath at proximal and distal ends of a tendon-sheath mechanism.
Figure 4:
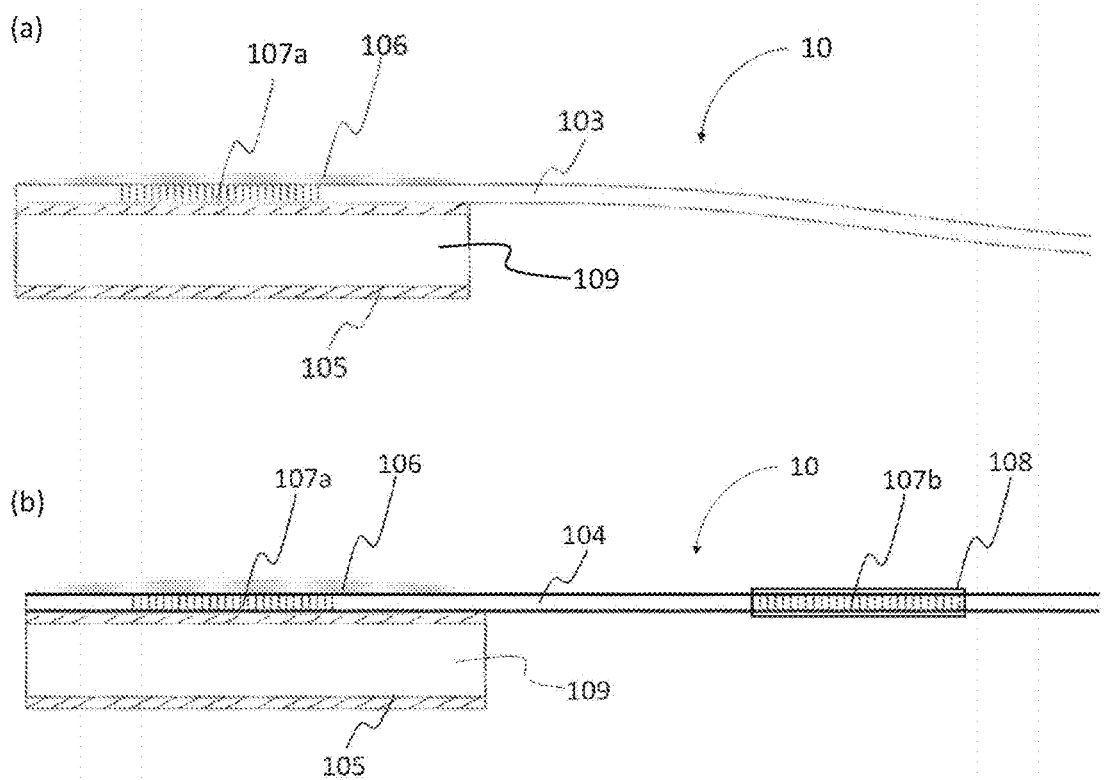
FIG. 4 is a schematic illustration of a first and second exemplary embodiments of a force sensor for tendon-actuated mechanisms.
Figure 5:
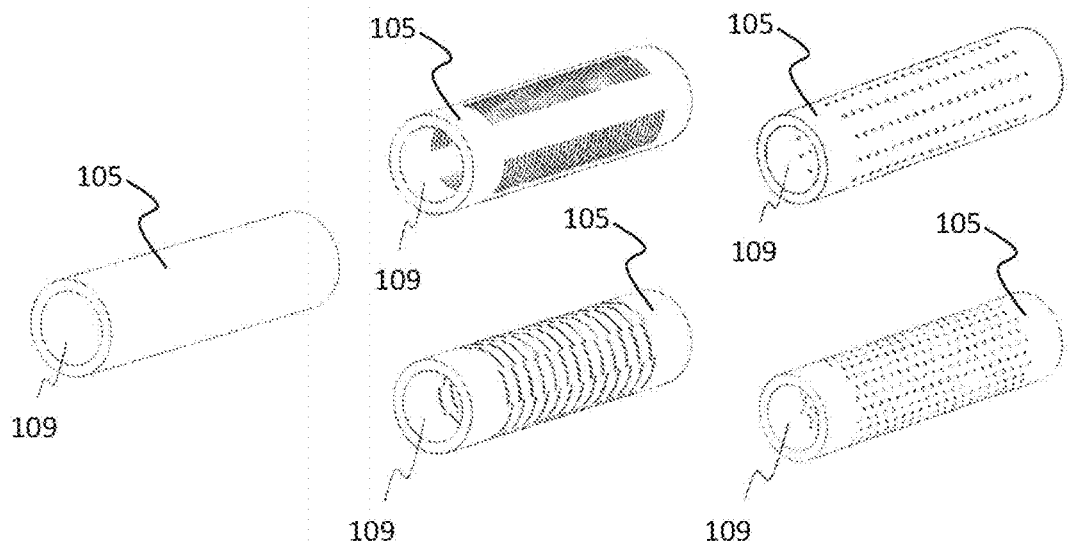
FIG. 5 shows exemplary embodiments of a body of the force sensor in the form of tubular structures of various designs.

Considering that the tendon of a TSM is much smaller than the sheath and moves and bends frequently, to avoid damage and to avoid decoupling elongation and bending, the presently disclosed force sensor measures the force on the sheath rather than that on the tendon, as a result of force analysis of TSM transmission system. FIG. 2 presents an infinitesimal segment of a tendon 102 and a sheath 101 of a TSM, both bent with a constant curvature, where T is the tension force on the tendon 102; C is the compression force on the sheath 101; N is the normal force from the sheath 101 to the tendon 102; f is the friction force applied by the sheath 101 to the tendon 102; N' is the normal force from the tendon 102 to the sheath 101; f' is the friction force applied by the tendon 102 to the sheath 101; α is the curve angle of this configuration; r is the radius of the curve in tendon-sheath configuration [26].

For the tendon, applying the force equilibrium equations for a small portion dx, with a corresponding angle da, the following four equations are obtained:

$$Td\alpha = -N,\ d\alpha = dx/r,\ f = \mu N \text{ and } dT = f; \tag{1-4}$$

where the loss of tension force is assumed to be caused only by the friction between the tendon and the sheath. Similar relationships also exist for the sheath:

$$Cd\alpha = -N',\ d\alpha = dx/r,\ f' = \mu N' \text{ and } dC = f'. \tag{5-8}$$

Based on Newton's Third Law, $$N = -N',\ f = -f'. \tag{9-10}$$

Thus, $$Td\alpha = -Cd\alpha. \tag{11}$$

Then, the crucial fundamental equations for this work are obtained:

$$T=-C;\ dT=-dC \quad (12\text{-}13)$$

The magnitude of the compression force on the sheath 101 thus equals that of the tension force on the tendon 102 at the same cross-section, i.e. $T=-C$.

This fact was further experimentally verified, where two load cells were applied to measure tension force on the tendon and compression force on the sheath at the proximal end and another two load cells were utilized to detect the tension force on the tendon and the compression force on the sheath at the distal end. A sinewave signal, with a frequency of 0.3 Hz and a converted motion amplitude of +1-90°, was sent to the motor (with a pulley diameter of 25 mm) to drive the tendon. Force readings from the four load cells are displayed in FIG. 3. The Root Mean Square Error (RMSE) between the tension force and the compression force was 0.618N for the proximal end and 0.332N for the distal end. These errors were mainly because of the noise of the load cells. Due to the limitation of experimental setup, the tendon could not be exactly parallel to the measuring axes of the load cells. The small misaligned angle resulted in a decomposition of the transmitted force, which may also lead to the error. The experiment result verified that the compression force of the sheath has almost the same magnitude as the tension force of the tendon at both the distal end and the proximal end. Thus, the relationship of the compression force and the tension force at any cross-section of the TSM, namely $T=-C$, is valid.

In a first exemplary embodiment of the force sensor 10, as shown in FIG. 4a, the force sensor 10 comprises a body 105 having a through hole 109 for passage of a tendon (not shown) of a tendon-actuated mechanism therethrough. The body 105 is configured to be connected to a part of the tendon-actuated mechanism through which the tendon passes. The force sensor 10 also comprises an optical fibre 103 having a first Fibre Bragg Grating (FBG) segment 107a, the first (and only) FBG segment 107a being attached to the body 105. In this embodiment, the body 105 comprises a tubular structure. The single FBG fibre 103 may be bonded with the tubular structure 105 using an epoxy 106 such as EPO-TEK 353ND. Additionally, a protection tube (not shown) can be applied to cover the force sensor 10 so that any abrasion/wearing from other sheaths can be prevented.

In a second exemplary embodiment of the force sensor 10 as shown in FIG. 4b, instead of attaching a single FBG fibre 103 to the body 105 (as shown in FIG. 4a), an optical fibre 104 comprising a first FBG segment 107a and a second FBG segment 107b (also referred to as a dual FBG array 104) may be used to include a temperature compensation feature. In the dual FBG array 104, the grating area or first FBG segment 107a (e.g. near the tip of the optical fibre 104) is stuck or attached to the tubular structure 105 for strain sensing while the other grating area or second FBG segment 107b is left strain-free by not being attached to any part of the tendon-actuated mechanism in order to offset any temperature effect on the FBG segments 107a. The strain-free grating area or second FBG segment 107b may be protected using a short outer tube 108 provided over the optical fibre 103 at the second FBG segment 107b. The distance between the two gratings or FBG segments 107a, 107b depends on the application of use of the force sensor 10. In general, the closer the two FBG segments 107a, 107b the better.

In an alternative embodiment (not shown), to offset the temperature effect, the force sensor 10 may comprise a temperature-independent FBG fibre which consists of an optical fibre having a first FBG segment that is temperature independent.

For all embodiments, the first FBG segment 107a is preferably set at the centre of the body 105. To secure the bonding where the body 105 comprises a tubular structure 105, length of the tubular structure 105 is preferably slightly longer than the length of the first FBG segment 107a to allow extra length of fibre to be glued to the tubular structure 105.

The body 105 of the force sensor 10 may be made of any deformable material, including metals such as steel or Nitinol, and polymeric materials such as liquid crystal polymer (LCP) or polyetheretherketone (PEEK), etc. Furthermore, to improve its flexibility and/or sensitivity, perforations such as slots or holes can be provided on the body 105, including but not limited to the various embodiments shown in FIG. 5.

Figure 6:
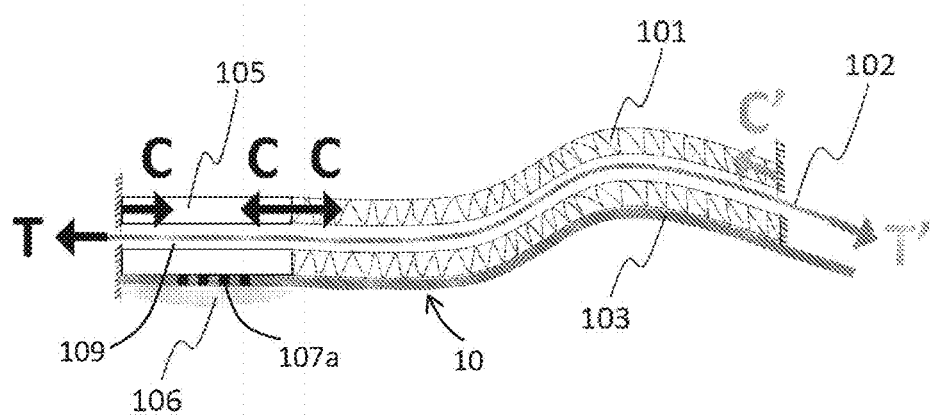
FIG. 6 is a schematic longitudinal sectional view of force analysis between a TSM and the body of the force sensor in the form of a tubular structure.

In use, the body 105 is attached to a part of the tendon-actuated mechanism through which the tendon passes, and shift in wavelength of light transmitted by the first FBG segment is directly correlatable to magnitude of a tension force applied to the tendon. FIG. 6 depicts the working principle of the force sensor 10 in an exemplary embodiment where the body 105 is a tubular structure and the tendon-actuated mechanism is a TSM that comprises a sheath 101 through which a tendon 101 passes. The force sensor 10 is connected to the sheath 101 by placing the tubular structure 105 at the distal end of the sheath 101 of the TSM, and the single FBG fibre 103 of the force sensor 10 is glued to the outer surface of the tubular structure 105 using an epoxy 106. To provide good contact, it is suggested to have similar outside diameters and inside diameters, or at least have an overlay contact area, for both the tubular structure 105 and the sheath 101. The tendon 102 of the TSM goes through both the sheath 101 and the tubular structure 105. When integrated with an end-effector 20 such as that shown in FIG. 7, the distal of the tubular structure 105 is also fixed to the end-effector 20. In this way, pulling on the tendon 102 at the proximal end of the TSM will result in a compression force from the sheath 101 to the tubular structure 105. This compression will further result in strain change in the first FBG segment 107a of the fibre 103, and the central wavelength will shift in the FBG reflected spectrum. Based on the wavelength shift, the compression force on the tubular structure 10 from the sheath 101 at the distal end can be calculated. Thus, the tension force on the tendon 102 at the distal end can be obtained based on $T=-C$.

By recording the wavelength shift of the first FBG segment 107a due to the strain experienced by the first FBG segment 107a as a result of the compression force on the body 105 from the sheath 101, the tension force magnitude on the tendon 102 which is equal or comparable to the compression force from the sheath 101 can thus be calculated. The real-time central wavelength shifts may be traced using an FBG Interrogator from providers such as Micron Optics (SM130 or SI255) and Smart Fibres, etc. For example, a first prototype embodiment of the force sensor 10 comprising a 1 mm-grating FBG fibre 103 attached to a 3 mm long super-elastic Nitinol tubular body 105 (outer diameter 1.27 mm and inner diameter 0.97 mm) was connected to a distal end of a sheath 101 (outer diameter 1.189 mm and inner diameter 0.72 mm) by placing one end of the body 105 in physical contact with the distal end of the sheath 101, and the FBG fibre 103 was then calibrated in four to five continuous tests, with a force ranging from 0 to 25N. To minimize the temperature cross-sensitivity, all the calibration experiments were carried out at constant room temperature. The calibration results are presented in FIG. 14 and FIG. 15. The first prototype embodiment force sensor 10 was found to have a sensitivity of 28.7 pm/N and an error of 0.174 N. A second prototype embodiment of the force sensor 10 comprising a 5 mm-grating dual array FBG fibre 104 attached to a 6 mm long super-elastic Nitinol tubular body 105 (outer diameter 1.27 mm and inner diameter 0.97 mm) was connected to a sheath 101 (outer diameter 0.965 mm and inner diameter 0.58 mm) by welding (e.g. laser welding) one end of the body 105 to a distal end of the sheath 101, and the FBG fibre 104 was then calibrated in similar tests to show a sensitivity of 34.7 pm/N and an error of 0.144 N. Such errors are within satisfactory level for most surgical tasks such as laparoscopy surgery, since they are below the sensitivity threshold of the human hand.

Furthermore, by utilizing a dual FBG array fibre 104 or temperature-independent FBG fibre, the force sensor 10 has an ability to offset the cross-influence of temperature in case there is great temperature change involved at the distal end of the surgical robot. The distance between two FBG gratings provided on one optical fibre of the force sensor depends on the application of use of the force sensor, although in general the closer the two FBGs are the better.

Figure 7:
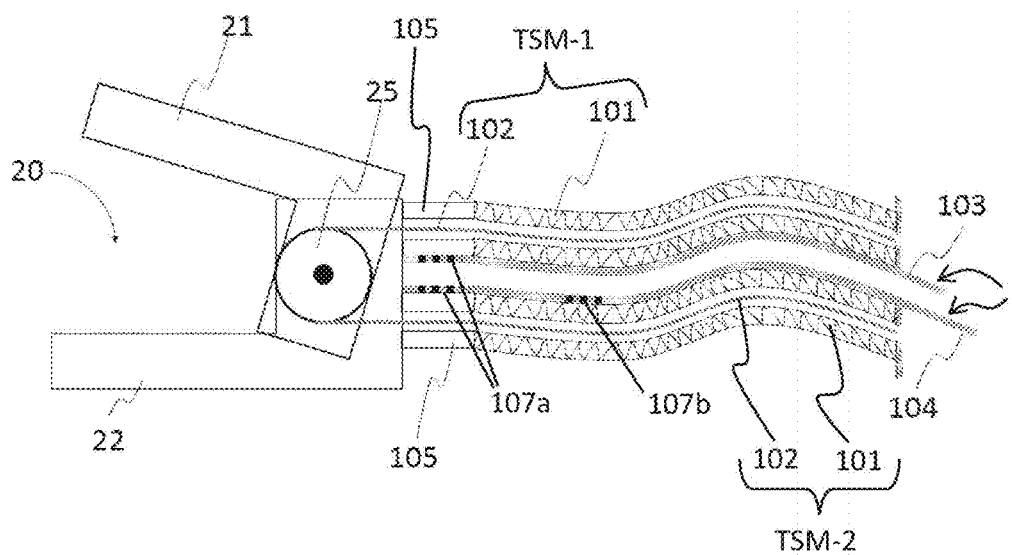
FIG. 7 is a schematic longitudinal sectional view of an integrated grasper actuated with a TSM provided with the force sensor with temperature compensation.

An exemplary implementation of the force sensor 10 in an end-effector 20 driven by two TSMs (TSM-1, TSM-2) for distal end haptic sensing is shown in FIG. 7. The end-effector 20 comprises a one-degree of freedom (1-DOF) grasper with two pivotally connected 25 jaws 21, 22 controlled by two TSMs. The lower jaw 22 cannot be rotated and thus also serves as a body structure 23 of the grasper. The upper jaw 21 can be bi-directionally rotated relative to the lower jaw 22 by two tendons 102 attached to the upper jaw 21. Each TSM is provided with one force sensor 10 of either the first exemplary embodiment shown in FIG. 4a or the second exemplary embodiment shown in FIG. 4b. Each tendon 102 extends from the upper jaw 21 through the tubular structure 105 of its associated force sensor 10 and sheath 101. The force sensor 10 can measure the compression force on its associated sheath 101 and thus the tension force on the associated tendon 102 can be obtained. In such a situation, one of the force sensors 10 may comprise a dual FBG array 104 which would be sufficient to compensate for any thermal expansion and contraction of the first FBG segment 107a. This 1-DOF grasper serves as an example only, and multiple force sensors can be used to trace distal end forces in a multi-DOF surgical instrument.

Figure 8:
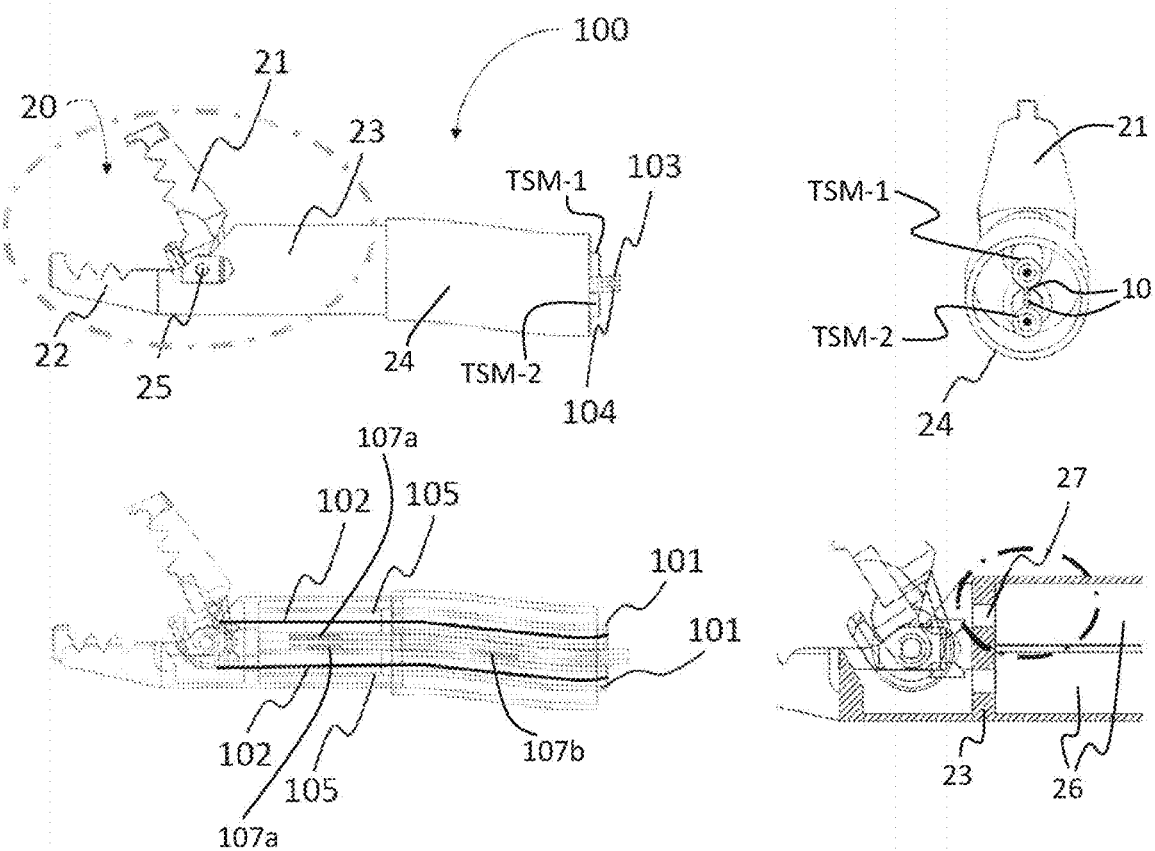
FIG. 8 is four views of a 3D grasper provided with the force sensor.

FIG. 8 shows an exemplary embodiment 100 of an end-effector 20 (grasper) integrated with the force sensors 10 and tendon-sheath driven mechanisms TSM-1, TSM-2 as described above with reference to FIG. 7. In this embodiment 100, each TSM comprises a sheath 101 of outer diameter 1.189 mm and inner diameter 0.72 mm, and a tendon 102 of outer diameter 0.4 mm. To each TSM is attached a force sensor 10 comprising a body 105 of a 3 mm long super-elastic body 105 of outer diameter 1.27 mm and inner diameter 0.97 mm (e.g. made of Nitinol), and an FBG fibre 103 or 104 having a 1 mm-long grating attached to the body 105. The body 105 of each force sensor 10 is attached to the distal end of each sheath 101 of the two TSMs. Both TSMs and attached force sensors 10 are covered by an over-tube 24 having an outer diameter of 4.4 mm. The body 105 of each force sensor 10 is inserted into a step hole 26 with a diameter of 2 mm that has a tendon outlet 27 at its distal end, the tendon outlet 27 having a diameter of 0.5 mm on the body structure 23 of the grasper 20. The sheath 101 is directly connected with the body 105 and a 1 mm long segment of the sheath 101 is provided inside the step hole 26 to secure good contact with the body 105.

Figure 9:
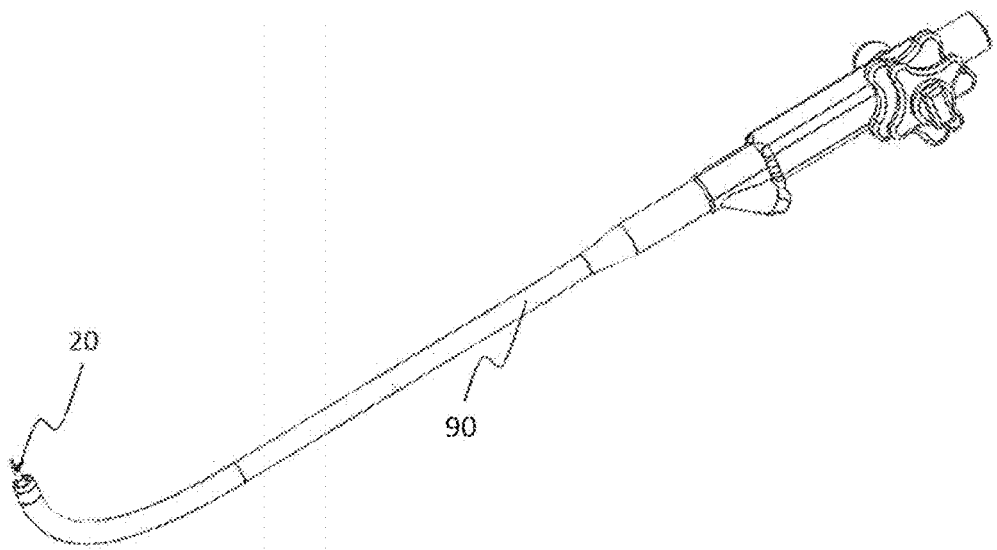
FIG. 9 is a perspective view of a 3D grasper provided in an endoscope.

FIG. 9 illustrates how the integrated-grasper 20 may be located in an endoscope 90. The presently disclosed force sensor 10 may thus be applied for use in a surgical robot with one or more tendon-sheath driven mechanisms for distal end force sensing with temperature compensation feature. Similarly, the force sensor 10 can also be used to obtain haptic feedback from the proximal end when it is integrated with proximal end devices. It should be noted that all the dimensions mentioned above are for example only and can be varied according to the needs of different applications as may be desired.

Figure 10A:
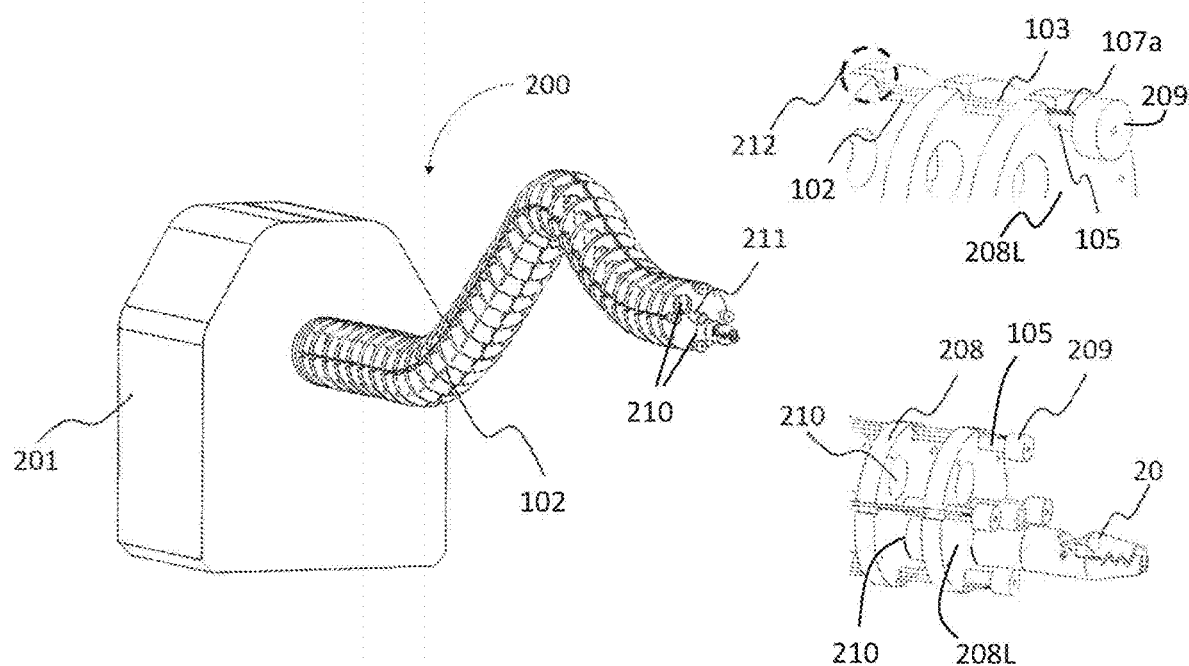
FIG. 10a is three perspective views of a tendon-driven mechanism in the form of a continuum robot provided with the force sensor.
Figure 10B:
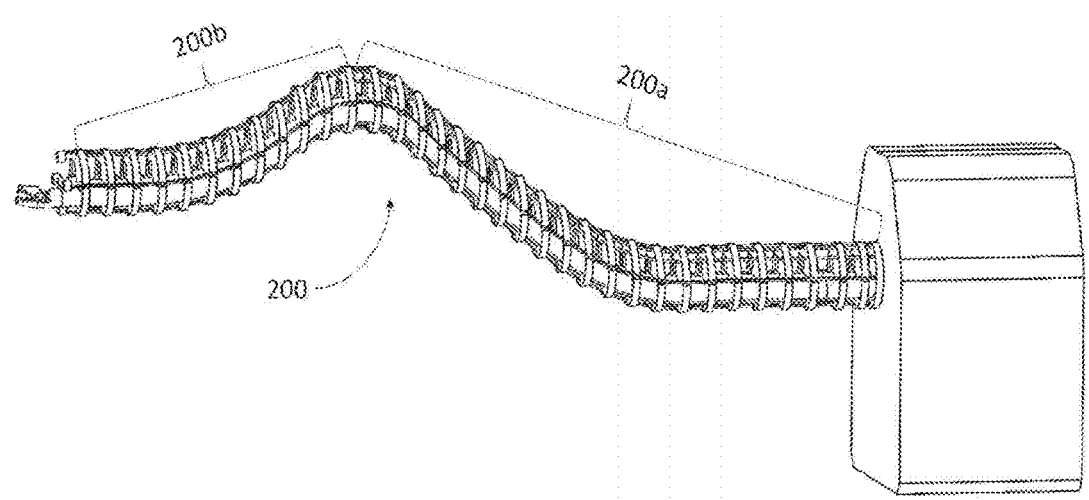
FIG. 10b is a perspective view of the continuum robot of FIG. 10a showing two segments of the robot.

In other embodiments of use of the force sensor 10, as shown in FIGS. 10a and 10b, the tendon-actuated mechanism may comprise a continuum robot 200 and the force sensor 10 is applied on the continuum robot 200. The continuum robot 200 is tendon-actuated with a tendon-driven mechanism that is integrated with the force sensor(s) 10 and provided with an end-effector 20 such as a grasper 20. The grasper 20 may itself also be provided with one or more force sensor(s) 10 as described above with reference to FIGS. 7 and 8. In the example shown in FIGS. 10a and 10b, the continuum robot 200 comprises a plurality of disks 208 having an outer diameter of 16 mm through which tendons 102 pass, a super-elastic spine 211 comprising a Nitinol tube having an outer diameter of 1.59 mm, the tendons 102 having an outer diameter of 0.3 mm that pass through the disks 208 and each terminate in a stopper 209, and an actuator housing 201 from which the disks 208 and tendons 102 extend. The continuum robot 200 is provided with two channels 210, each channel 210 comprising a series of through holes having a diameter of 4.4 mm provided in the plurality of disks 208 to offer space for an end-effector 20 to pass through the disks 208. It should be noted that all the dimensions mentioned above are for example only and can be varied according to the needs of different applications as may be desired.

In this embodiment, the continuum robot 200 has two segments 200a and 200b as shown in FIG. 10b, with two degrees-of-freedom (2-DOF) at the first segment 200a and another 2-DOF at the second segment 200b. In total eight tendons 102 are provided and be driven to perform the 4-DOF movements. Four of the eight tendons 102 will stop at the end of the segment 200a while the remaining four tendons 102 will continue to pass through segment 200b. The number of segments and tendons in any continuum robot is not limited to two and in other embodiments (not shown) this can be more. The force sensor(s) 10 are integrated with the robot 200 for distal force detection on each tendon 102 by providing the body 105 of each force sensor 10 as a tubular structure between the stopper 209 and the disk 208L immediately adjacent the stopper 209. The stopper may have an outer diameter of 2.5 mm, or any other appropriate diameter that is larger than the external diameter of the body 105. Slots 212 are provided at the edge of the disks 208 to allow passage of the FBG fibres 103 therethrough.

Figure 11:
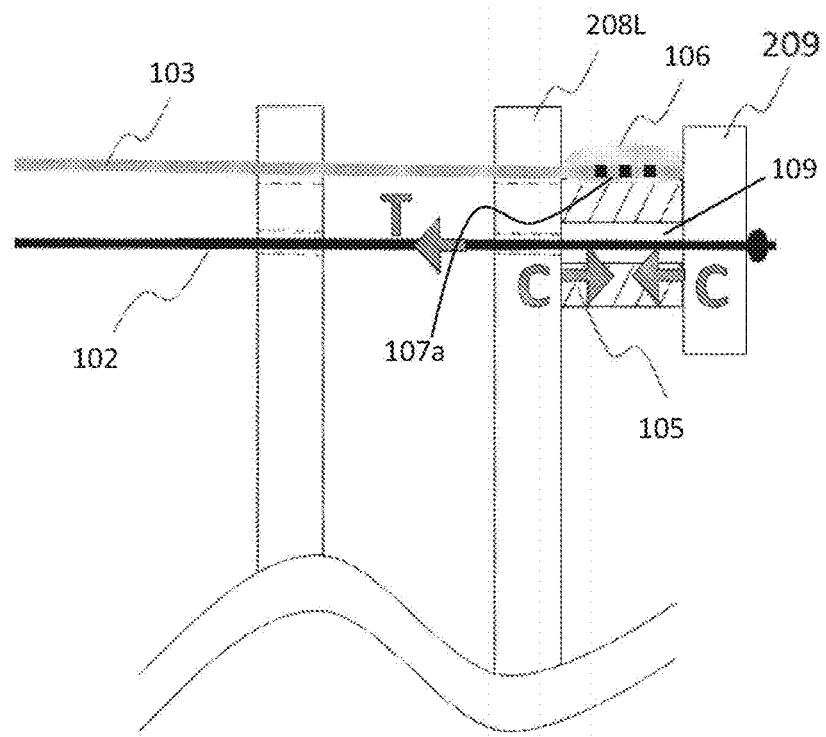
FIG. 11 is a schematic longitudinal sectional view of force analysis in the continuum robot of FIG. 10a between disks of the continuum robot, the body of the force sensor in the form of a tubular structure, and a stopper at a distal end of the continuum robot.

In the embodiment of the continuum robot 200 described above, the force sensor(s) 10 can be implemented for distal end haptic feedback at any tendon 102 of interest in the continuum robot 200, even for the tendons 102 that end at the distal end of the first segment 200a. FIG. 11 shows a schematic illustration of the force analysis when a tendon 102 of the continuum robot 200 is pulled. As a result of the tension in the tendon 102, the tubular structure 105 between the last disk 208L and the stopper 209 is compressed, with a compression force equal to the tension in the tendon 102 as established above. Change in strain experienced by the FBG segment 107a due to compression on the tubular structure 205 will be captured and transmitted by the FBG fibre 103 and used to obtain the tension force in the tendon 102. The FBG fibre 103 may be replaced by a dual FBG array fibre (not shown) to include temperature compensation as a feature. Alternatively, a temperature-independent FBG fibre may be used. In this way, presently disclosed force sensor 10 can also be applied into a flexible robot with tendon-driven mechanism for distal end force sensing with temperature compensation feature.

Figure 12:
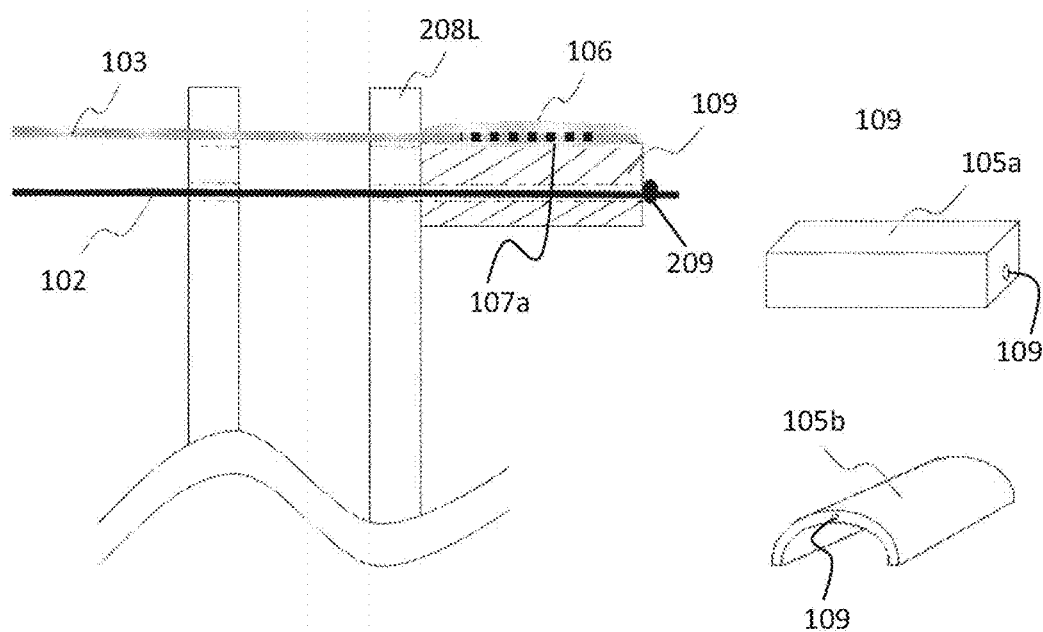
FIG. 12 shows exemplary embodiments of the body of the force sensor in alternative forms.

In other embodiments, instead of the body 105 of the force sensor 10 comprising a tubular structure as described in the above examples, the body 105 may alternatively comprise other structural configurations such as a beam 105a or a shell (i.e. a longitudinal section of a cylinder) 105b as shown in FIG. 12 that is provided with a through hole 109 for passage therethrough of the tendon of a tendon-driven flexible robot for haptic feedback.

Figure 13:
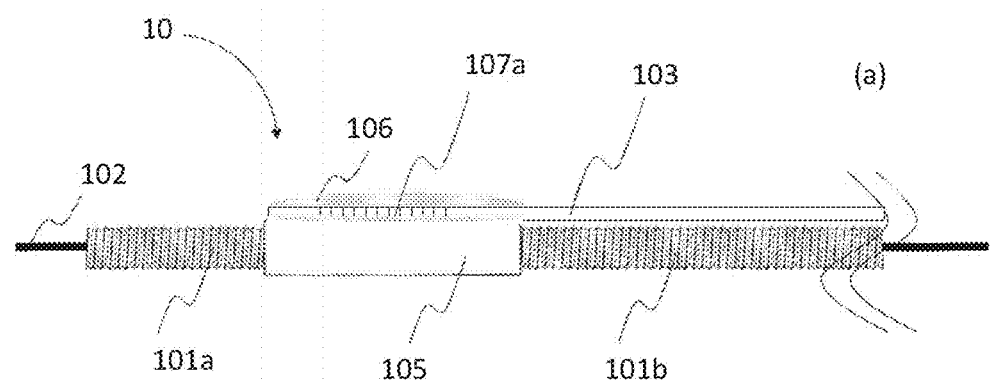
FIG. 13 shows alternative configurations of provision of the force sensor in a TSM.
Figure 13:
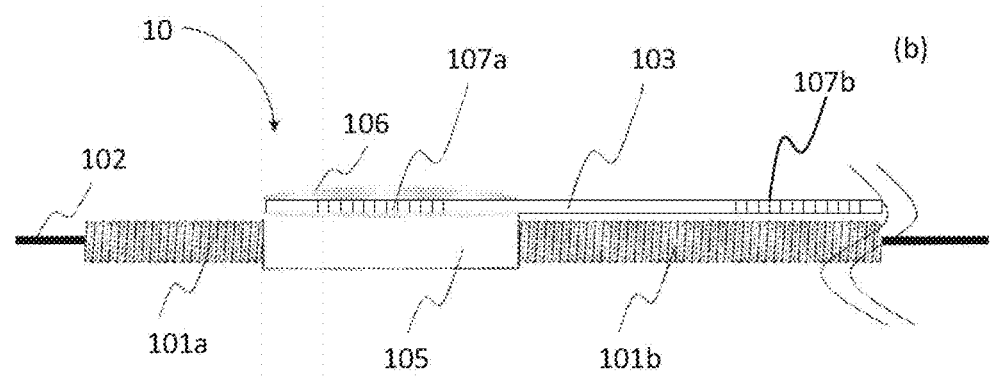
Figure 14:
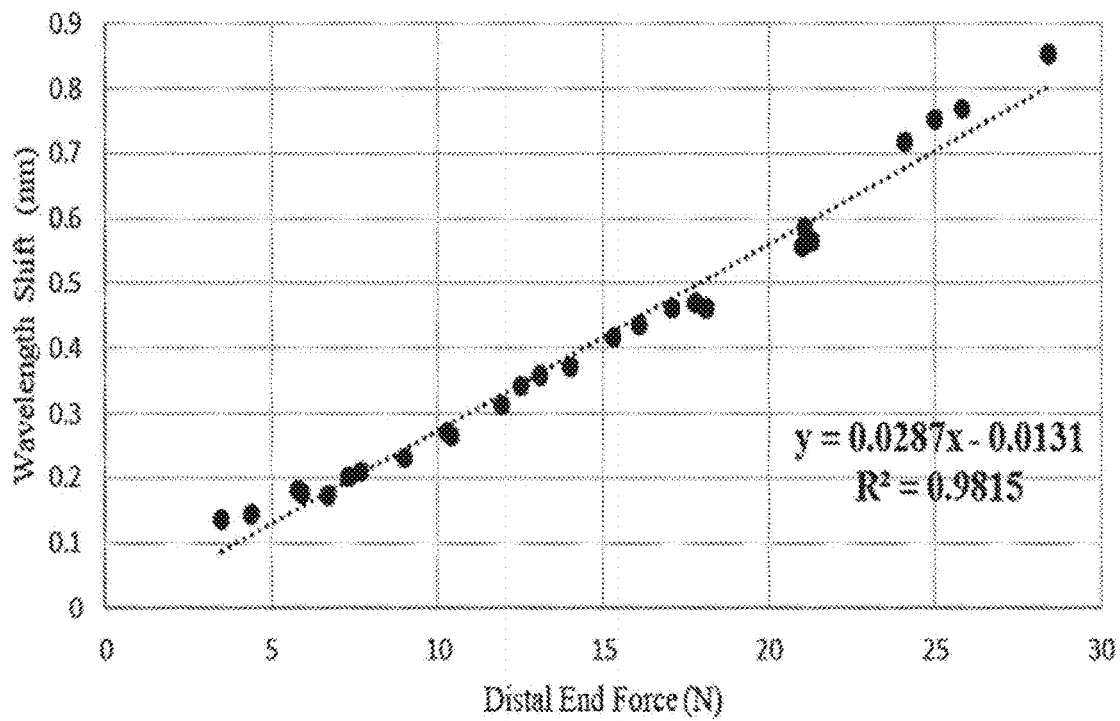
FIG. 14 is a graph of calibration results of a first exemplary prototype of the force sensor.
Figure 15:
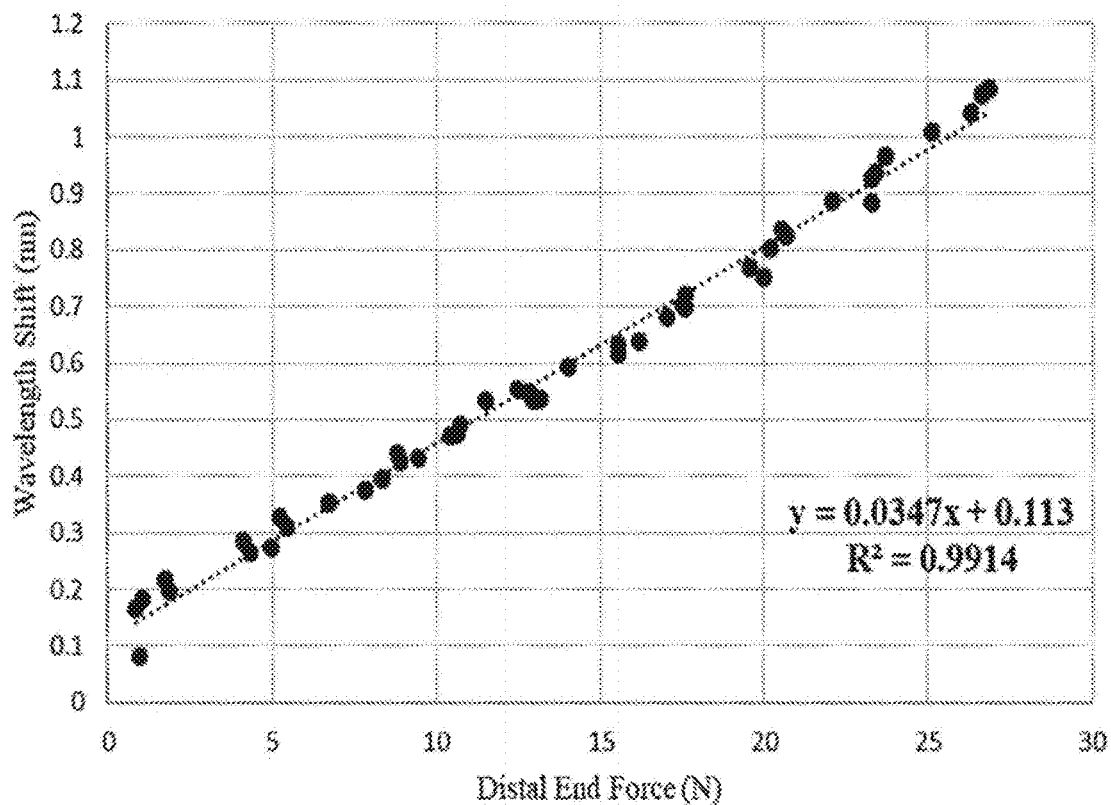
FIG. 15 is a graph of calibration results of a second exemplary prototype of the force sensor.

In further exemplary configurations of use, instead of providing the force sensor 10 at one end of the sheath of a TSM, the force sensor 10 may alternatively be provided such that the body 105 of the force sensor 10 is located between two sheaths 101a and 101b, which is considered more compact and has less restriction for the sensor length. As shown in FIG. 13, the body 105 of the force sensor 10 in the form of a tubular structure is set between the two sheaths 101a and 101b, with similar dimensions and hollow configuration between the body 105 and the sheaths 101a, 101b. In one example as shown in FIG. 13a, a first (and only) FBG segment 107a of a single FBG fibre 103 is adhered to the tubular structure 105 using a suitable epoxy 106 (such as EPO-TEK 353ND), with the grating area 107a at the middle of the body 105. By pulling the tendon 102, the sheaths 101a and 101b and the body 105 come into physical contact with each other. Through the force transmission, the equal relationship between the tension force on the tendon 102 and the compression force on the sheaths 101a and 101b is still valid. In another example as shown in FIG. 13b, the force sensor 10 comprises a dual array FBG fibre 104 having a first FBG segment 107a attached to the body 105 and a strain-free second FBG segment 107b that is not attached to any part of the tension-actuated mechanism to offset the temperature cross-sensitivity. Alternatively, a temperature-independent FBG fibre (not shown) may be used.

In the configurations shown in FIG. 13, it is easy to disassemble and assemble the force sensor 10 from the TSMs. Also, the location of the tubular structure 105 may be freely determined depending on the application of use of the TSM. These configurations are preferred when multi-TSMs are involved in a system since the location of the tubular structure 105 can be allocated at separated positions on different sheaths 101a and 101b to avoid contact conflict between multiple force sensors 10. Additionally, the tubular structure 105 can be laser welded to the sheaths 101a and 101b if contact security is a priority. Notably, welding is not the only way to affix the tubular structure 105 with sheaths 101a and 101b as other bonding methods such as adhesives may alternatively be used.

The present force sensor 10 described above thus provides a miniature force sensor integrated with one or more Fibre Bragg Gratings (FBGs) for flexible endoscopic robots with optional temperature-compensation feature. In addition to an endoscopic robot with tendon-sheath driven mechanisms, the disclosed force sensor 10 can also be applied to detect the distal end haptic information in a tendon-driven continuum robot. In addition to distal end force sensing, the force sensor 10 can also be used to obtain haptic feedback at the proximal end or in-between the mechanisms.

For haptic sensing of TSMs, the present force sensor 10 measures the compression force on the sheath 101 so that the tension force on the tendon 102, which equals the compression force on the sheath 101, can be obtained. In the experiments conducted, it was confirmed that the compression force on the sheath 101 and the tension force on the tendon 102 at the same cross-section of a tendon-sheath mechanism are equal in magnitudes. The corresponding verification experiment result is present in FIG. 3.

By measuring the total force applied to the end-effector (e.g. grasper) through the transmission mechanism (such as the TSM or continuum robot), the present force sensor 10 avoids the problem of force decoupling compared to mounting sensors directly on the end-effector. The present force sensor thus requires no need for the decoupling of forces in different directions on the end-effector nor the decoupling of elongation and bending on tendons, while allowing for compact integration with TSMs, wiring simplicity, electrical passivity, and MRI-compatibility. The present force sensor therefore has advantages such as small size, high sensitivity and resolution, dismount ability, multi-mechanism transferability, temperature compensation, flexibility, easy-fabrication, and ability to be sterilized. The present force sensor may be applied for a variety of either TSMs-driven or tendon driven systems, such as robotic fingers/hands, wearable devices, surgical catheters, and rehabilitation devices.

Whilst there has been described in the foregoing description exemplary embodiments of the present invention, it will be understood by those skilled in the technology concerned that many variations and combination in details of design, construction and/or operation may be made without departing from the present invention. For example, while it has been described above that the force sensor is provided with one or more FBG strain sensor where strain detected by the FBG on the body is correlatable to compression force on the body from the part of the tendon-actuated mechanism through which the tendon passes, in alternative embodiments of the force sensor, the compression force on the body may be detected using other sensors such as a MEMS (Micro Electro Mechanical Systems) force sensor or MEMS strain sensor that allows detected strain to be correlated to the magnitude of compression force on the body.

REFERENCES

[1] S. J. L. Phee, S. C. Low, K. Y. Ho, and S. C. Chung, "Robotic system for flexible endoscopy," U.S. Pat. No. 8,882,660, Nov. 11, 2014.

[2] S. Ehrampoosh, M. Dave, M. A. Kia, C. Rablau, and M. H. Zadeh, "Providing haptic feedback in robot-assisted minimally invasive surgery: A direct optical force-sensing solution for haptic rendering of deformable bodies," *Computer Aided Surgery*, vol. 18, pp. 129-141, 2013/09/01 2013.

[3] A. M. Okamura, "Haptic Feedback in Robot-Assisted Minimally Invasive Surgery," *Current opinion in urology*, vol. 19, pp. 102-107, 2009.

[4] Y. Kobayashi, P. Moreira, C. Liu, P. Poignet, N. Zemiti, and M. G. Fujie, "Haptic feedback control in medical robots through fractional viscoelastic tissue model," in 2011 *Annual International Conference of the IEEE Engineering in Medicine and Biology Society*, 2011, pp. 6704-6708.

[5] E. R. Morales and C. C. Salvador, "Force estimation for a minimally invasive robotic surgery system," U.S. Pat. No. 9,855,662, Jan. 2, 2018.

[6] T. N. Do, T. Tjahjowidodo, M. W. S. Lau, and S. J. Phee, "A new approach of friction model for tendon-sheath actuated surgical systems: Nonlinear modelling and parameter identification," *Mechanism and Machine Theory*, vol. 85, pp. 14-24, 2015 Mar. 1.

[7] M. Kaneko, T. Yamashita, and K. Tanie, "Basic considerations on transmission characteristics for tendon drive robots," in *Advanced Robotics*, 1991. 'Robots in Unstructured Environments, 91 ICAR., Fifth International Conference on, 1991, pp. 827-832 vol. 1.

[8] L. Chen and X. Wang, "Modeling of the tendon-sheath actuation system," in 2012 19th *International Conference on Mechatronics and Machine Vision in Practice (M2VIP)*, 2012, pp. 489-494.

[9] P. Puangmali, K. Althoefer, L. D. Seneviratne, D. Murphy, and P. Dasgupta, "State-of-the-Art in Force and Tactile Sensing for Minimally Invasive Surgery," *IEEE Sensors Journal*, vol. 8, pp. 371-381, 2008.

[10] T. V. Selkee, "Catheter having a force sensing distal tip," U.S. Pat. No. 8,374,670, Feb. 12, 2013.

[11] R. Heinrich and D. J. Cuny, "Surgical instruments including mems devices," U.S. Pat. No. 8,808,311, Aug. 19, 2014.

[12] R. Heinrich and D. J. Cuny, "Surgical instrument including MEMS devices," U.S. Pat. No. 9,561,031, Feb. 7, 2017.

[13] J. Talarico, D. Mihai, and D. Rathburn, "Gentle touch surgical instrument and method of using same," U.S. Ser. No. 11/242,304, Apr. 5, 2007.

[14] A. A. G. Abushagur, N. Arsad, M. Ibne Reaz, A. Ashrif, and A. Bakar, "Advances in Bio-Tactile Sensors for Minimally Invasive Surgery Using the Fibre Bragg Grating Force Sensor Technique: A Survey," *Sensors (Basel, Switzerland)*, vol. 14, pp. 6633-6665, 2014.

[15] K. O. Hill and G. Meltz, "Fiber Bragg grating technology fundamentals and overview," *Journal of Lightwave Technology*, vol. 15, pp. 1263-1276, 1997.

[16] S. J. Blumenkranz and D. Q. Larkin, "Force and torque sensing for surgical instruments," U.S. Pat. No. 8,945,095, Feb. 3, 2015.

[17] G. Leo, N. Aeby, and D. Inaudi, "Medical apparatus system having optical fiber load sensing capability," U.S. Pat. No. 8,075,498, Dec. 13, 2011.

[19] G. Leo, N. Aeby, and D. Inaudi, "Medical apparatus system having optical fiber load sensing capability," U.S. Pat. No. 8,182,433, May 22, 2012.

[19] G. Leo, N. Aeby, and D. Inaudi, "Medical apparatus system having optical fiber load sensing capability," U.S. Pat. No. 8,932,288, Jan. 13, 2015.

[20] G. Leo, N. Aeby, and Y. Vanenkov, "Temperature compensated strain sensing catheter," U.S. Pat. No. 8,298,227, Oct. 30, 2012.

[21] G. Leo, "Elongated surgical manipulator with body position and distal force sensing," U.S. Pat. No. 8,622,935, Jan. 7, 2014.

[22] D. Q. Larkin and D. C. Shafer, "Robotic surgery system including position sensors using fiber bragg gratings," U.S. Pat. No. 7,930,065, Apr. 19, 2011.

[23] B. S. Ramamurthy, N. A. Tanner, R. G. Younge, and R. L. Schlesinger, "Robotic instrument systems and methods utilizing optical fiber sensor," U.S. Pat. No. 9,186,046, Nov. 17, 2015.

[24] J. M. Zand and G. S. Fischer, "Surgical instruments with sensors for detecting tissue properties, and system using such instruments," U.S. Pat. No. 9,204,830, Dec. 8, 2015.

[25] P. S. Zarrin, A. Escoto, R. Xu, R. V. Patel, M. D. Naish, and A. L. Trejos, "Development of an optical fiber-based sensor for grasping and axial force sensing," in 2017 *IEEE International Conference on Robotics and Automation (ICRA)*, 2017, pp. 939-944.

[26] Z. Wang, Z. Sun, and S. J. Phee, "Haptic feedback and control of a flexible surgical endoscopic robot," *Computer Methods and Programs in Biomedicine*, vol. 112, pp. 260-271, 2013 Nov. 1.

[27] J. O. Zhi Zhou, "Techniques of temperature compensation for FBG strain sensors used in long-term structural monitoring," 2004.

The invention claimed is:

1. A force sensor for a tendon-actuated mechanism, the force sensor comprising: a body having a through hole for passage of a tendon of the tendon-actuated mechanism therethrough, the body configured to be connected to a part of the tendon-actuated mechanism through which the tendon passes; and a sensor provided on the body, wherein the body is compressible longitudinally in response to a tension force axially along the tendon resulting from pulling of the tendon; wherein the sensor is configured to obtain a compression force longitudinally along the body resulting from compression of the body longitudinally; wherein the compression force is comparable to the tension force, such that the tension force axially along the tendon is measured based on the compression force longitudinally along the body.

2. The force sensor of claim 1, wherein the sensor comprises an optical fibre having a first Fibre Bragg Grating (FBG) segment, the first FBG segment being attached to the body, and wherein shift in wavelength of light transmitted by the first FBG segment is directly correlatable to the compression force longitudinally along the body.

3. The force sensor of claim 2, wherein the optical fibre has a second FBG segment, wherein in use, the second FBG segment is not attached to any part of the tendon-actuated mechanism and shift in wavelength of light transmitted by the second FBG segment is directly correlatable to a difference in temperature experienced by the second FBG segment.

4. The force sensor of claim 2, wherein the first FBG segment is attached to an outer surface of the body.

5. The force sensor of claim 2, wherein grating length of the first FBG segment is less than or equal to 1 mm.

6. The force sensor of claim 1, wherein the body is made of a deformable material.

7. The force sensor of claim 1, wherein the body is provided with perforations to improve flexibility of the body.

8. The force sensor of claim 1, wherein the body comprises a tubular structure.

9. The force sensor of claim 1, wherein the tendon-actuated mechanism comprises a tendon-sheath mechanism, wherein the part of the tendon-actuated mechanism comprises a sheath of the tendon-sheath mechanism, and wherein the body is collinearly attached to the sheath of the tendon sheath mechanism.

10. The force sensor of claim 9, wherein the part of the tendon-sheath mechanism comprises at least two sheaths of the tendon-sheath mechanism, and wherein the body of the force sensor is provided between the at least two sheaths.

11. The force sensor of claim 1, wherein the tendon-actuated mechanism comprises a continuum robot, the continuum robot comprising a plurality of disks and a number of tendons passing through the plurality of disks, at least some of the number of tendons each terminating in a stopper, wherein for at least one of the number of tendons terminating in a stopper, the body of the force sensor is provided between the stopper and a disk that is immediately adjacent the stopper.

12. A method of determining a force on a tendon-actuated mechanism, the method comprising:
   a) providing a force sensor on a part of the tendon-actuated mechanism through which a tendon of the tendon-actuated mechanism passes, the force sensor comprising a body and a sensor provided thereon;
   b) passing the tendon through a through hole of the body;
   c) generating a tension force axially along the tendon resulting from pulling of the tendon;
   d) compressing the body longitudinally in response to the tension force;
   e) obtaining with the sensor a compression force longitudinally along the body resulting from compression of the body longitudinally, wherein the compression force is comparable to the tension force; and
   f) measuring the tension force axially along the tendon based on the compression force longitudinally along the body.

13. The method of claim 12, wherein the sensor comprises an optical fibre having a first Fibre Bragg Grating (FBG) segment attached to the body, and wherein step e) comprises obtaining a shift in wavelength of light transmitted by the first FBG segment and correlating the shift in wavelength of light transmitted by the first FBG segment to magnitude of the compression force longitudinally along the body.

14. The method of claim 13, further comprising:
   g) providing a second FBG segment not attached to any part of the tendon-actuated mechanism;
   h) obtaining a shift in wavelength of light transmitted by the second FBG segment;
   i) correlating the shift in wavelength of light transmitted by the second FBG segment to a difference in temperature experienced by the second FBG segment; and
   j) offsetting the shift in wavelength of light transmitted by the first FBG segment with the shift in wavelength of light transmitted by the second FBG segment to compensate for difference in temperature experienced by the first FBG segment.

* * * * *